United States Patent [19]

Polaschegg et al.

[11] Patent Number: 4,508,622
[45] Date of Patent: Apr. 2, 1985

[54] DIALYSIS APPARATUS WITH REGULATED MIXING OF THE DIALYSIS SOLUTION

[75] Inventors: Hans-Dietrich Polaschegg, Oberursel; Dieter Husar, Bad Homburg, both of Fed. Rep. of Germany

[73] Assignee: Fresenius AG, Bad Homburg, Fed. Rep. of Germany

[21] Appl. No.: 506,154

[22] Filed: Jun. 20, 1983

[30] Foreign Application Priority Data

Jun. 21, 1982 [DE] Fed. Rep. of Germany ....... 3223051

[51] Int. Cl.³ ...................... B01D 13/00; B01D 31/00
[52] U.S. Cl. .................................. 210/96.2; 210/321.2
[58] Field of Search ............................ 210/96.2, 321.2

[56] References Cited

U.S. PATENT DOCUMENTS

| 3,352,779 | 11/1967 | Austin et al. | 210/96.2 |
| 3,506,126 | 4/1970 | Serfass et al. | 210/96.2 |
| 3,697,418 | 10/1972 | Johnson | 210/195 |
| 4,137,168 | 1/1979 | Perrot | 210/96.2 |
| 4,153,554 | 5/1979 | Heide | 210/96.2 |
| 4,366,051 | 12/1982 | Fischel | 210/96.2 |
| 4,388,184 | 6/1983 | Brous | 210/96.2 |
| 4,399,036 | 8/1983 | Babb et al. | 210/96.2 |

FOREIGN PATENT DOCUMENTS 2644584 4/1978 Fed. Rep. of Germany .
3215824 11/1982 Fed. Rep. of Germany .

OTHER PUBLICATIONS

Von H. Schneider, "Elektrolytbilanz bei Hanodialyse und Hamofiltration," *Medizintechnik* 101 (1981), 5, pp. 121–123.

H. G. Sieberth et al., "Methodische und Klinische Probleme des Natriumstoff Wechsels unter der Chronischen Dialyse Behandlung", (N.D.), Third Symposium of Innsbruck, 1969, pp. 206–214.

*Primary Examiner*—John Adee
*Attorney, Agent, or Firm*—Townsend and Townsend

[57] ABSTRACT

A dialysis apparatus having a unit for the production of the dialysis solution and a dialyzer includes a first detector mounted upstream of the dialyzer and a second detector mounted downstream of the dialyzer by means of which the composition of the dialysis solution can be regulated. The measuring data of detectors are compared and eventually used to control the composition of the dialysis solution; the invention is particularly useful in high exchange capacity dialyzers, since the composition of the dialysis solution can be adjusted directly and at any time to maintain desired conditions in the dialyzed patient.

17 Claims, 4 Drawing Figures

DIALYSIS APPARATUS WITH REGULATED MIXING OF THE DIALYSIS SOLUTION

BACKGROUND OF THE INVENTION

1. Field of the Invention

This invention concerns dialysis equipment, namely a dialysis apparatus with a unit to produce a dialysis solution from a concentrate and water.

Dialysis equipment of the described kind is already known. It usually contains a conductivity cell as a detector mounted upstream of the dialyzer in order to measure the temperature-compensated conductivity value of the dialysis solution thereby to indicate a change in the electrolyte contents of the dialysis solution.

The detector itself serves not only to adjust the electrolyte contents of the dialysis solution, but also to switch off the entire device if the latter causes a critical condition in the patient. To regulate the electrolyte composition of the dialysis solution, the conductivity cell used as detector controls a pump which pumps the concentrate from a concentrate storage tank into the mixing unit. The mixing unit, on the other hand, is equipped with a tap water connection through which controlled water is supplied. In the mixing unit itself, water and concentrate are mixed and heated under control so that the desired composition of the dialysis solution is obtained at the outlet of said unit.

This dialysis solution is routed through the dialyzer, wherein the blood is cleared of urinary substances and fluid is withdrawn.

Because of the high exchange capacity of modern dialyzers, urinary substances are removed very rapidly from the blood and the dialysis time is thus reduced. Thus, in highly effective dialyzers, the treatment time can be reduced to 3×2 hours a week, within which not only the urinary substances such as urea but also excessive fluid are removed.

The withdrawal of the excess fluid demands a very precise control of the fluid balance, requiring that this process take place only with fluid-balancing devices. Despite precise balancing, the patients still experience some typical undesirable dialysis side effects such as headache, vomiting and muscle cramps designated as "disequilibrium syndrome." The reason is probably the excessively rapid withdrawal of sodium ions from the blood based on the difference of sodium concentration in the blood (extracorporal circulation) and in the dialysis solution. The higher the exchange capacity of the dialyzer, the lower may be the admissible gradient of sodium concentration between blood and dialyzing solution. Thus, a difference of a maximum of 10 nmol/l sodium should be admissible for normal dialyzers, reduced to one half this value in high-performance dialyzers.

However, the sodium contents in the patient's blood differs and is commonly still outside of normal range of 135–147 nmol/1. In order to prevent the above-described dialysis symptoms, it is advisable to work with a sodium concentration of about 144 nmol/1 in the dialysis solution. The consequence is that the patient becomes thirsty during the treatment and accumulates relatively large amounts of liquid until the next dialysis treatment and is thus over-watered. It is not unusual to observe excess weight of up to 6 kgs. This added liquid must then be ultrafiltered during the treatment time of about 2–3 hours to withdraw the required quantity of sodium with this volume of liquid. In fact, however, this prior method of treatment is not sufficiently precise to entirely prevent the above symptoms during treatment.

Furthermore, the excessive over-watering which occurs between treatments is not at all good for the organ, yet it can hardly be avoided with the methods of the prior art.

2. Description of the Prior Art

Devices have already been developed (e.g., SERATRON of Cordis-Dow) which, based on a dialysis solution with predetermined composition, change the composition during the time of dialysis, said change taking place in accordance with a set program. The process is known as "sodium modelling." This program has, of course, the disadvantage that it is not at all tailored to individual requirements. Due to the fixed preprogrammed concentrations, difficulties will arise in patients with differing sodium levels. Besides, this program does not take into account the differences between the exchange capacity of the various dialyzers, so that even here disequilibrium symptoms cannot be avoided.

The prior art has been of the opinion that a determination of sodium elimination during dialysis would be impossible, since even at a very low measuring error of 1%, there could be over the duration of the dialysis a high absolute deviation, i.e., a sodium loss or increase. Accordingly, determination of sodium elimination in dialysis was abandoned (see H. G. Sieberth, et al., "Modern Problems of Dialysis Processes and Kidney Insufficiency," 3rd Symposium Innsbruck 1969, pp. 206–214, especially pg. 211, §3).

Due to such measuring difficulties, the prior art in general has operated with certain predetermined compositions of the dialysis solution which were either constant or variable in accordance with a certain program (sodium modelling). Consequently, to this date patients have necessarily been subjected to a determined composition of the dialysis solution instead of adapting the composition to the patient, since the latter was not believed possible.

SUMMARY OF THE INVENTION

According to the present invention a dialysis device is provided of the above kind in which the electrolyte composition of the untreated and treated fluids routed through the dialyzer can be determined and eventually the composition of the dialysis solution adapted to the patient's requirements.

The solution of this problem is attained according to the claimed features of the invention, and in particular by providing a first electrolyte detector upstream of the dialyzer and a second electrolyte detector downstream of the dialyzer, each detector coupled to a readout element through which both of the values of the dialysis solution can be observed and eventually controlled. It was found unexpectedly that the electrolyte contents of the fluids circulating through the dialyzer, i.e., of the blood and dialysis solution, can in fact be so accurately determined with an electrolyte detector upstream of the dialyzer and another downstream of it that the composition of the dialysis solution can be suitably controlled and accurately adjusted to the patient's needs.

According to a first embodiment, an evaluation unit is provided in combination with the two above-mentioned detectors which in an attached differential unit, i.e., a comparator, can indicate the difference of the composition of the electrolyte contents differentially as well as integrally for certain predetermined times. Thus, the difference of the electrolyte contents of fluids circulating through the dialyzer can be controlled and integrally maintained for the time of the dialysis treatment.

According to a second embodiment, the value determined by the readout and differentiation unit can be used to control the composition of the dialysis solution so that the electrolyte metabolism of the patient is adjusted to the value desired by the physician. Thus, the composition of the dialysis solution will be regulated so that the electrolyte composition of the patient's blood usually corresponds to that of a healthy individual, i.e., an individual not suffering from kidney deficiency. On the other hand, a special electrolyte composition could be induced at which the patient usually feels comfortable and is thus not subject to metabolic disturbances.

The dialysis device according to this invention operates as follows. With the dialysis device according to said invention, the electrolyte concentration can first of all be predetermined for the dialysis solution with which the patient is first treated. A similar, first-determined dialysis solution enters the dialyzer and is used in the dialyzer for exchange purposes along the dialysis membrane. If said dialysis solution shows a difference in the concentration of the electrolytes from that of the blood on the inlet side, said concentration difference is reduced in a high-exchange capacity dialyzer to a difference of about 5% by the time the blood is let out. This latter difference is due to the plasma anions present in the blood which are less able to penetrate the semipermeable membrane of the dialyzer. The residual difference is thus about 5% of the absolute concentration and is explained by the Gibbs-Donnan Theory.

It has already been shown that a similar concentration difference is usually undesirable in the dialysis treatment of a patient, since, as above explained, significant changes in the electrolyte metabolism of the patient lead to the unpleasant symptoms of disequilibrium.

Therefore, the concentration of the electrolytes in the dialyzing solution is measured at the outlet of the dialyzer with a second detector, the above-mentioned concentration difference obtained at the outlet of the dialyzer being taken into consideration. The value obtained at the dialyzer outlet differs from the value obtained at the dialyzer inlet for the concentration of the dialysis solution if there is a concentration difference of electrolytes between dialysis solution and blood. Thus, by supplying the two values obtained by measuring the electrolyte concentrations upstream and downstream of the dialyzer into the regulation unit according to this invention, the mixing unit, and especially its pump which pumps the concentrate into said mixing device, can be controlled.

Thus, according to this invention, the electrolyte concentration during dialysis can be continuously regulated to a certain value or in accordance with a chronological sequence of values, said control being based directly upon the electrolyte concentration in the blood. This regulation offers the advantage that, as distinguished from the control schemes heretofore employed, the electrolyte concentration in the blood is the reference and control value.

Fortunately, it is sufficient for the production of the dialysis solution to use only a concentrate solution diluted at the rate of about 1:34 with water. Usually, as explained in the introduction, the concentration of the dialysis solution will vary during dialysis treatment by at most ±8%, so that the influence upon the other electrolytes, i.e., potassium or calcium, is practically insignificant.

On the other hand, variable concentrations with different electrolytes can be used, where each concentrate tank is connected to a pump through which the predetermined quantity of each concentrate is fed into the mixer. The pumps themselves are governed by controls connected to ion-selective sensors or detectors. With a similar ion-selective sensor, the specific concentration of a certain electrolyte can be determined and regulated independent of other electrolytes.

In yet another embodiment a sensor or detector is provided for determination of the total electrolyte contents upstream and downstream of the dialyzer. Advantageously, these two sensors are each connected with an adjacent temperature sensor. Temperature sensors provide temperature compensation for the parameters measured, e.g., of the electrochemical potentials or conductivity. However, to the extent to which the temperature of the dialysis solution corresponds to the body temperature of the patient, temperature compensation may be omitted.

The sensors are connected to an actual value device which, in turn, is connected with a preprogrammed reference value device. If the actual value deviates from the reference, the composition of the dialysis solution is corrected by adjusting the pump carrying the concentrate solution to the mixing unit until the actual value coincides with the reference value.

In order to determine the total ion concentration, either the conductivity measurement or the determination of ion potentials, particularly sodium ions, can be advantageously carried out by means of ion-selective electrodes. The latter method has the advantage over the former that several types of ions can be measured selectively and adjusted with the aid of the device according to this invention. On the other hand, the electrodes applied are much more unstable and breakable than the ion-conductivity cell, so that the conductivity measurements are preferred for normal dialysis.

In addition, ion-selective electrodes show a potential drift if they are exposed to variable pressures, e.g., vacuum used to produce ultrafiltration on the side of the dialysis fluid in the dialyzer. Accordingly, in another embodiment this behavior is taken into account and the measurement is made with pressure compensation. For this purpose, branch lines are provided upstream and downstream of the dialyzer on the lines of the dialysis solution which can be blocked by means of shut-off devices.

Synchronized with these shut-off devices is at least one pump downstream which overcomes the vacuum prevailing in the line of the dialysis solution. The pump is connected to the measuring unit consisting of at least one detector. According to this embodiment, the measurements are alternate, i.e., the detector is applied alternately to treated and untreated dialysis solution.

In yet another embodiment, at least one of the above-mentioned detectors can be provided also in the extracorporal blood circulation at the dialyzer. In particular, a sensor may be provided at the inlet and one at the outlet of the dialyzer in the extracorporal circulation.

In addition, the sensors provided in the extracorporeal circulation can be separated from the blood by plasma filters, i.e., they can receive only plasma which essentially contains the electrolytes to be determined.

These measurements can be made either in on-line operation, or blood specimens can be taken from the extracorporal circulation paths by means of lines connected to the extracorporal circulation paths and which are closable with metering valves.

Additional characteristics, details and embodiments of the invention are explained in the description hereafter, making reference to the drawings.

IN THE DRAWINGS

DETAILED DESCRIPTION OF THE PREFERRED EMBODIMENTS

Figure 1:
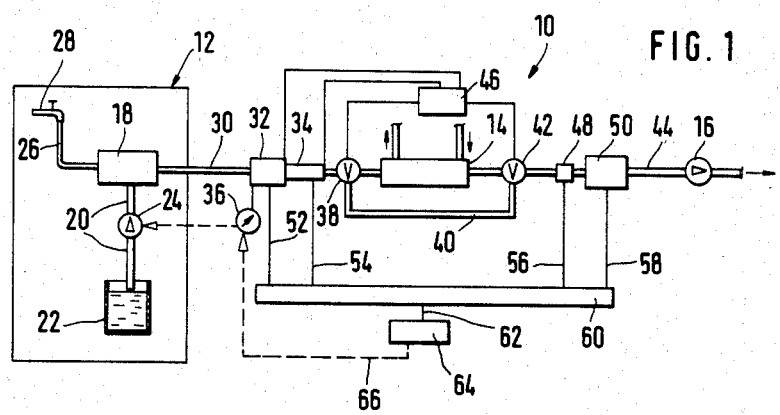
FIG. 1 is a schematic representation of a first embodiment of a dialysis apparatus with a detector upstream and a detector downstream of the dialyzer in the dialysis solution line.

FIG. 1 shows a dialysis apparatus 10. The dialysis apparatus consists essentially of a unit 12 for production of the dialysis solution and a dialyzer 14 connected with unit 12, followed downstream by a pump 16 to produce a vacuum in the dialyzer on the side of the dialysis fluid.

Unit 12 is simplified; its main component is a mixing unit 18 (not detailed) which is connected through line 20 to a tank 22 containing concentrate solution. In line 20 a controllable pump 24 is provided in order to feed the concentrate into the mixing unit 18.

The mixing unit 18 is also connected via line 26 to a fresh water supply 28. The water arriving in the mixing unit 18 is heated by a heater (not shown) to about the body temperature of the patient. The pump 24 is operative to draw concentrate from tank 22 which is then mixed in the mixing unit with the heated tap water.

In the mixing unit 18, the excess gas dissolved in the dialyzing solution is separated. Otherwise gas would be released in the dialyzer 14 where a certain vacuum prevails.

From mixing unit 18 line 30 routes the dialysis solution to the dialyzer 14. A first detector 32 is provided in line 30 which will measure at least one concentration parameter of the electrolytes contained in the dialysis solution. Normally, this will be the concentration of sodium salts, since the latter makes up at least 90% of the conductivity value. Preferably, however, the sum of all concentrate parameters will be measured, since all concentrations are commonly present in the same proportions. This is due to the fact that only one type of concentrate solution is used.

As explained hereafter, the use of a concentrate solution containing such a mixture of all electrolytes is nevertheless not necessarily mandatory. Thus, it is possible for the electrolyte salt to be present in the form of a concentrate which is fed into the mixing unit 18 through a feeder system corresponding essentially to line 20 and pump 24. A sodium salt, particularly sodium chloride, could preferably be present in the form of its concentrate and the other electrolytes in another concentrate. Nevertheless, much preferred is the use of a specified concentrate as shown in FIG. 1, since the change of no more than 10% sodium-ion concentration in the dialysis fluid during the dialysis results in a relative change of the same order for the other electrolytes, which can be tolerated by the organism without much trouble.

Detector 32 mounted upstream of the dialyzer 16 also measures a concentration parameter of the dialysis solution. If a conductivity detector is used as detector 32—which is the detector type preferred—the conductivity of the total dialysis solution is measured. The measured value obtained is compensated with the aid of a temperature detector 34 mounted downstream of the detector 32. Detector 32 may be further connected with a control unit 46 which can control pump 24 according to the measured value determined by detector 32.

Downstream of the temperature detector 34, a bypass valve 36 is mounted in line 38 from which a line 30 is connected to dialyzer 14 and to a bypass line 40. The bypass line 40 is connected to another bypass valve 42 mounted downstream of the dialyzer in line 44. Both bypass valves are electrically connected to the control unit 46 which is also electrically connected to detector 32 and to the temperature detector 34. If the temperature of the measuring value measured at detector 32 deviates from the nominal value, control unit 46 activates the bypass valves so that the incompletely conditioned dialysis fluid is routed through the bypass line 40, bypassing dialyzer 14. This prevents the dialysis fluid of the wrong composition or temperature from getting into the dialyzer. However, once the composition and temperature of the dialysis fluid are completely conditioned, the fluid is routed to the dialyzer 14 and subsequently through another temperature detector 48 and detector 50 wherein at least one concentration parameter in the dialyzing liquid can again be measured. The detectors 48 and 50 are, according to the invention, mounted downstream of dialyzer 14 in line 44. The pump 16 is downstream of detectors 48 and 50. The pump 16 produces a predetermined vacuum in the conduit system leading from unit 12 to pump 16 for the purpose of controlling ultrafiltration.

Detectors 32, 34, 48 and 50 are connected through signal lines 52, 54, 56 and 58 respectively with a comparator or evaluation unit 60 which is connected by a signal line 62 to a differentiation unit 64. As shown in dotted line 66, a control signal is provided by the differentiation unit 64 to control unit 36 if there is a difference in the differentiation unit 64 which deviates from the predetermined nominal value.

The embodiment shown in FIG. 1 operates as follows. In unit 12, a dialyzing solution is formulated in the conventional manner. When said dialyzing solution leaves unit 12, the bypass valves 38 and 42 are switched to the bypass position until detector 32 shows the fixed predetermined concentration. (This switching can, however, be changed by overriding the difference unit 64.)

Once the desired dialyzing solution is attained, it is pumped by pump 16 through dialyzer 14 under a vacuum, the bypass valves 38 and 42 having been switched. At this point the control of the contents of the dialysis solution commences according to this invention. If detector 50 generates a signal to the readout or evaluation unit 60 and subsequently to the differentiation unit 64 which deviates by a certain amount from the signal generated by detector 32, i.e., a difference in value appears which deviates from the predetermined value for differentiation unit 64, the difference unit 64 activates the control unit 36 as shown at 66, which in turn switches 24 on or off as a function of the higher or lower concentration in the dialysis solution to be produced.

The difference in the differentiation unit 64 is so selected that a difference in concentration of the sodium ions contained in the dialysis solution upstream and downstream of the dialyzer is no more than 5 nmol/l, preferably not more than 1–2 nmol/l, being set especially around 0 nmol/l. Actually, if no difference is determined upstream and downstream of the dialyzer, the ultrafiltrate drawn from the blood by dialyzer 14 will show practically the same electrolyte composition as the blood itself, which is generally desired.

In a further refinement of the embodiment shown in FIG. 1, the bypass valves 28 and 42 as well as bypass line 40 can be used to check the detectors 32, 34, 48 and 50. Detectors 32 and 50 and 34 and 48 can be compared with each other by pumping pure dialysis solution through lines 30, 40 and 44 bypassing the dialyzer. Under such conditions where tests are carried out frequently, e.g., every 10–15 minutes, the respective values of the detectors in the evaluation unit 60 are set at zero so that absolute calibration of the detectors used is superfluous, and only an identical dependency of the detectors on concentration is required.

After calibration, i.e., after the respective switching of the bypass valves 38 and 42, normal dialyzing of the patient resumes. The dialyzing liquid diverted from the pump 16 is routed into the drain.

All detectors which can be used to determine ion concentration in liquids are suitable as detectors 32 and 50. This applies to conductivity measurement, electrochemical measurement of individual types of ions or total spectrographic measurement, magnetic measurement and similar. Among the detectors preferably used are the conductivity cell and ion-selective electrodes.

The use of a conductivity cell is known in today's traditional dialysis apparatus. Thus, a conductivity detector is used to supervise the predetermined conductivity value upstream of the dialyzer used only for supervision of a predetermined value. Regulation of said value is also provided by the state of technology through the above-mentioned sodium modelling which does not make reference to prevailing conditions resulting from the electrolyte concentration in the patient and dialyzer used. Ion-selective electrodes are also known, e.g., from Cammann "Work with Ion-Selective Electrodes," 2nd edition, 1977, Springer-Verlag, Berlin, and from D-PS 2215378 which is incorporated herein by reference and made a part hereof. Similar ion-selective electrodes are made of an ion-exchange material which is active with either cations or anions. Among such materials are, e.g., quarternary ammonium groups, phosphonium ions or sulphonium ions which could have organic radicals. Also long-chain aliphatic mercaptans, alkylated phenols or macrocyclic ethers, e.g., crown ethers. It is, in particular, possible, to create membrane electrodes which respond to alkali ions and contain complexes of cron ether or analogous compounds, particularly valinomycines.

Besides, two-value or multiple value ions can be determined so that practically any possible metal ion can be measured.

Among additional cation-sensitive materials we find metal chelates, ion-exchange salts or ion-exchange materials. Especially favored for the measurement of potassium ions is valinomycine, for the measurement of sodium ions a dioxasuberic acid diamide, for calcium ions also a dioxasuberic acid diamide derivative which differs from the above-mentioned diamide. On the other hand, sodium ions can also be determined with a Na-selective glass which is preferred over the ion-selective electrodes on an organic basis, because of its robustness. The pH value can also be determined with a pH-selective glass electrode which again is available on the market and has been described in D-AS 2134101 to which reference is made for disclosure reasons.

Ion-selective electrodes of an organic basis are usually made in the form of thin membranes of PVC material to which a softener has been added. Similar polymer materials and the manufacture as well as addition of softeners are described, e.g., in D-PS 2215378 to which reference is made.

A similarly manufactured ion-selective electrode is connected with the traditional branching, e.g., an electrolyte solution as connector (saturated KCL-solution) with a deflector electrode which, in turn, is connected to a traditional measuring and amplifying device, in this invention is called evaluation unit 60.

In accordance with the embodiment shown in FIG. 1, detectors 32 and 50 of the same composition are preferred, i.e., either conductivity cells or ion-selective electrodes.

Due to the fixed relative composition of the concentrate solution contained in tank 22, the total composition of the dialysis liquid can be controlled with a sodium-selective electrode.

Figure 2:
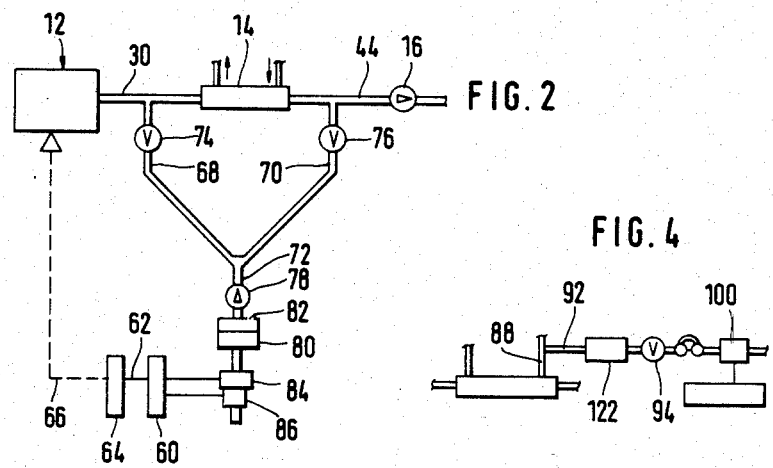
FIG. 2 is a schematic view of another embodiment with a branching in the dialysis solution line each upstream and downstream of the dialyzer, the branch lines leading to a detector.

FIG. 2 shows another embodiment of the invention using identical reference symbols for like elements. The embodiment shows again a unit 12 to produce a dialysis liquid. From the unit 12 a line 30 is directly connected with the dialyzer and subsequent line 44. Lines 30 and 44 each have a branch line 68 and 70 combined into a line 72. Preferably, line 68 is mounted directly upstream and line 70 directly downstream of dialyzer 14.

Since pump 16 produces a vacuum in lines 30 and 44 of the dialysis solution, lines 68 and 70 are closed by shut-off devices 74 and 76 and will preferably be opened and closed alternately. To draw fresh or used dialysis solution into line 72, pump 78 is provided in said line 72 which overcomes the vacuum in lines 30 and 44. A storage tank 80 is mounted at the pump in which pressure compensation is made, e.g., through an opening 82 in tank 80. Downstream of storage tank 80, detector 84 is mounted which in function and composition corresponds to detectors 32 and 50 and which is temperature-compensated by a temperature detector 86. Coupled to said detectors 84 and 86 is again an evaluation unit 60 with the conventional controls. As can be seen in the embodiment of FIG. 2, this embodiment operates with only one detector exposed alternately to fresh or used dialysis solution, thus making do with only one detector. This embodiment too is considered to come within the scope of the invention. In fact, for constant control of the total composition of the dialysis solution, no further detector is required in line 30 leading directly to the dialyzer. However, this line 30 would preferably have a similar detector, corresponding to the detector 32 shown in FIG. 1, in particular a conductivity cell which can immediately detect any major variation in the dialysis solution, so that operation of the dialysis apparatus can be stopped.

In accordance with this preferred embodiment, a conductivity cell can be mounted in line 30, while an ion-selective electrode could be used as detector 84, which is calibrated by alternate operation with continually fresh dialysis solution, and which is operative to determine only the difference between the used dialysis solution pumped through line 70 and the fresh dialysis solution. A similar embodiment shown in FIG. 2 has the advantage that modern dialysis equipment can be supplemented with an external detection device, especially an ion-selective measuring set. The conduit system connected to the dialyzer 14 merely needs to be provided two connections for lines 68 and 70. On the other hand, of course, a conventional conductivity cell can be used as detector 84.

Figure 4:
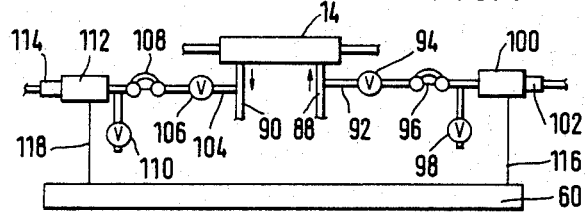
FIG. 4 is another schematic view of an embodiment similar to the embodiment of FIG. 3.
Figure 3:
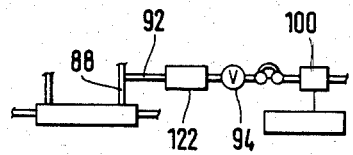
FIG. 3 is a schematic view of a third embodiment showing, in addition to the embodiments of FIGS. 1 and 2, detectors provided in the extracorporal blood circulation path.

The embodiments shown in FIGS. 3 and 4 are specific enhancements of the embodiments shown in FIGS. 1 and 2, and thus must be considered in connection with the latter. For the sake of simplicity, the respective instruments provided in the dialysis circulation path have been omitted.

According to the embodiment shown in FIG. 3, the blood circulation of dialyzer 14 is connected with at least one detector which can determine the electrolyte conditions, conductivity, hematocrit value or pH of the blood.

Dialyzer 14 has an extracorporal line 88 for the blood supply and a line 90 for discharge of blood from dialyzer 14. A line 92 branches line 88 in which a shut-off device is mounted. Subsequently, there is a pump 96, preferably a hose pump. Downstream of the pump an escape valve 98 is provided adjacent to line 92 for pressure compensation of the blood in line 92. Subsequently, in line 92 is the detector 100 which in type, composition and structure corresponds to detectors 32 and 50 and which preferably can be temperature-compensated by temperature detector 102.

In another embodiment also shown in FIG. 3, line 90 also shows a branch line 104 containing a shut-off device 106, a pump 108, a relief valve 110 and detectors 112 and 114. The drainage follows the last-named detector.

The embodiment shown in FIG. 3 operates as follows. By means of shut-off devices 94 and 106 opened at certain time intervals or continuously kept open, a relatively small quantity of blood is drawn by pump 96. Downstream of the pump, the blood in line 92 is pressure-compensated so that the pressure-sensitive measurement with ion-selective electrodes (if any of these are used) is not disturbed or altered. The data resulting from detectors 100 and 102 is provided via signal line 116 or 118 to the evaluation unit 60.

The measuring values are then processed according to the process for the device in FIG. 1.

A preferred embodiment consists of the apparatus of FIG. 1 or 2 combined with the one in FIG. 3 and branched either on line 88 or line 90 so that only one of the measuring sets according to FIG. 3 is used. Otherwise, the embodiment of FIG. 3 can essentially be structured in accordance with FIG. 2, so that the shut-off devices 94 and 106 correspond to the shut-off devices 74 and 76, and detectors 100, 102, 112 and 114 are combined in one detector corresponding to detectors 84 and 86. This device then operates like the device in FIG. 2, i.e., alternately, since only one of the shut-off devices is open or closed, while at the same time the other shut-off device is closed or open.

In the embodiment shown in FIG. 4, which for the sake of simplicity shows only one branch 92 in line 88, a hemofilter 122 is provided upstream of the shut-off device 94 to filter the plasma from the blood corpuscles so that only the plasma is subject to measurement by detector 100. The rest of the arrangement according to FIG. 4 corresponds to the arrangement in FIG. 3. Thus, the embodiment according to FIG. 4 is changed from the one in FIG. 3 in that a hemofilter 122 is mounted in line 92 whereby the blood plasma can be adjusted to the desired values.

The embodiment in FIG. 3 permits measurement of the electrolytes contained in the blood as well as hematocrit value which is measured by means of conductivity and is a parameter with which the water withdrawal from the patient can be determined. It increases with increasing water withdrawal from the patient and thus indicates which quantity has been ultra-filtered. In addition, a certain increased hematocrit value measured preferably by means of a conductivity cell as detector 100 or 112 shows a critical value from which the patient could go on into the so-called hypovolemic shock, once the tolerance limits of volume withdrawal have been reached. Accordingly, such increase in the hematocrit value can be used to control ultra-filtration and to increase the safety margin of similar equipment.

This combination of the embodiments of FIGS. 3 and 4 with those of FIGS. 1 and 2 offers the advantage that more than one detector makes up the measuring system, so that, in the formation of a mean value, the precision and thus the sensitivity of the entire system is enhanced by a factor $\sqrt{n}$, n being the number of detectors applied.

On the other hand, however, the embodiment shown in FIG. 3 with a measurement set at the inlet and outlet of blood in the dialyzer 14 may be sufficient by itself for precision regulation of the composition of the dialysis solution, i.e., the combination with the embodiments shown in FIGS. 1 and 2 may not be required.

In another preferred embodiment it has been found that it is preferable to have a detector 32 and a control unit 36 controlling pump 24 and thus the flow of concentrate, to first prepare and then control the lower electrolyte composition still able to be tolerated by a patient, e.g., a dialysis solution with a sodium content of 135 nmol/1. In this embodiment another line corresponding to line 20 from tank 20 and another pump corresponding to pump 24 are mounted for precision regulation of the composition of the dialysis solution. This additional pump is also controlled by a unit corresponding to control unit 36 and by the differentiation unit 64. This embodiment offers the advantage that supervision and precision regulation of the dialysis solution do not overlap or are not separated from each other. In this case, the detector 32 can be provided either alone or with another detector upstream of the dialyzer 14 having the same or different characteristics as detector 32.

The above description refers to dialysis apparatus which fall under the concept of "devices for cleansing of blood." To this extent, a similar application of the invention is not limited to dialysis alone but extends to any other device for cleansing of blood, e.g., hemofiltration. In hemofiltration, plasma is filtered in a hemofilter from the quasi solid components of the blood. In this case, the hemofilter used corresponds to the above-mentioned dialyzer 14. In hemofiltration, the substitution solution is recombined with the blood downstream of the hemofilter according to the volume of plasma withdrawn. In this case, according to the embodiments of the invention shown in FIGS. 1 to 4, a detector is provided at the blood inlet and another at the blood outlet of the hemofilter, as well as a detector at the plasma discharge, according to a first embodiment.

The admixture of substitution solution takes place again in the form of a concentrate which is used to make up the substitution. Instead of similar concentrates, of course, pre-mixed solutions can be used, the composition of which corresponds to the lower value able to be tolerated by a patient. Again, the composition formed with the concentrate is precision-regulated as above where, e.g., the difference of the measured values at the blood inlet and outlet or the absolute value at the plasma outlet are measured. On the other hand, however, blood inlet and plasma outlet values can be compared.

With a similar hemofiltration apparatus it is possible to change or adapt the composition of the substitution solution in direct operation according to the conditions prevailing during hemofiltration.

It may be further noted that each of the above-explained devices for cleansing of blood can have up to four measuring points connected with at least one detector. In a similar embodiment, the measuring points are scanned according to a predetermined switching method and evaluated in one or more differentiation units.

It must further be pointed out that the evaluation unit 60 and eventually the differentiation unit 64 can be used to measure the electrolyte concentrations of untreated and treated fluids routed through the dialyzer. Thus, for instance, the electrolyte concentration at the inlet and outlet of dialyzer 14 can be directly measured and the difference of said values determined and indicated differentially and integrally over a certain period of time.

According to such an embodiment, there is no change in composition of the dialyzing solution by respective control of unit 12 to produce the dialyzing solution.

Thus, this embodiment is a mere measuring device for measuring and differential and/or integral indication of the electrolyte balance, especially the sodium balance.

The invention has been explained with reference to specific embodiments. Other embodiments will be apparent to those of ordinary skill in the art. Therefore, it is not intended that this invention be limited except as indicated by the appended claims.

What is claimed is:

1. A dialysis apparatus with a unit for the production of a dialysis solution from a concentrate and water, the apparatus having a concentrate tank, a mixing unit, a pump for feeding concentrate from the concentrate tank into the mixing unit and a water connection connected to the mixing unit, the apparatus having a dialyzer for producing a treated liquid, said dialyzer being connected with said mixing unit, said dialyzer being equipped with two dialyzer chambers separated by a membrane, the first dialyzer chamber being adapted to be filled with blood, the apparatus further having pumps to route blood and untreated dialysis liquid through the dialyzer, and an ultrafiltration device to produced ultrafiltrate for withdrawal characterized in that:

an evaluation unit is provided at least for observation of a comparison of a representation of electrolyte contents of untreated liquid and treated liquid directed through said dialyzer;

at least one first detector is provided which is connected to receive untreated liquid upstream of said dialyzer and which is connected with said evaluation unit, said first detector being operative for determining and conveying to said evaluation unit a representation of the electrolyte contents of untreated liquid upstream of said dialyzer; and at least one second detector is provided which is connected to receive treated liquid downstream of said dialyzer and which is connected with said evaluation unit, said second detector being operative for determining and conveying to said evaluation unit a representation of the electrolyte contents of treated liquid downstream of said dialyzer.

2. The apparatus according to claim 1, wherein said first and second detectors are each combined with a temperature detector.

3. The apparatus according to claim 1, further including a unit for forming a difference value wherein said evaluation unit is connected with said difference value forming unit.

4. The apparatus according to claim 3, wherein said difference value forming unit is connected with said control unit by means of which said dialysis solution producing unit can be controlled.

5. The apparatus according to claim 1, wherein a first bypass valve is mounted between said first detector and said dialyzer and a second bypass valve is provided between said second detector and said dialyzer and said first and second bypass valves are connected to a bypass line.

6. The apparatus according to claim 5, further including temperature detectors associated with said respective first and second detectors wherein said first and second detectors and said temperature detectors can be calibrated with fresh dialysis solution by activating said first and second bypass valves.

7. The apparatus according to claim 1, comprising:
a line (92) and a line (88), said line (92) being branched on said line (88) leading to a blood inlet side of said dialyzer; and
a line (104) and a line (90), said line (104) being branched on said line (90) leading away from said dialyzer, containing a shut-off valve, a pump, said line 92 and said line 104 a relief valve and said first or second detector.

8. The apparatus according to claim 7, wherein upstream of said shut-off valve at least one hemofilter is provided.

9. The apparatus according to claim 1, wherein first or second detector comprise a conductivity cell and at least an ion-selective electrode.

10. The apparatus according to claim 9, wherein said ion-selective electrode is a sodium selective, potassium-selective, pH-selective, $SO_2$, $CO_2$, $HCO_3$-sensitive and/or calcium-selective electrode.

11. The apparatus according to claim 1, wherein values measured by said first and second detectors can be indicated by means of said evaluation unit differentially and/or integrally.

12. A dialysis apparatus with a unit for the production of a dialysis solution from the concentrate and water, the apparatus having a concentrate tank, a mixing unit, a pump for feeding concentrate from the concentrate tank into the mixing unit, and a water connection connected to the mixing unit, the apparatus having a dialyzer for producing a treated liquid, said dialyzer being equipped with two dialyzer chambers separated by a membrane, the first dialyzer chamber being adapted to be filled with blood, the apparatus further having pumps to route blood and untreated dialysis liquid through the dialyzer, and an ultrafiltration device to produce ultrafiltrate for withdrawal, characterized in that:
   an evaluation unit is provided at least for observation of a comparison of a representation of electrolyte contents of untreated liquid directed into said dialyzer and treated liquid exiting from said dialyzer; and
   a detector is provided for determining electrolyte contents of liquids passing through said dialyzer, said detector being alternately connected to receive untreated liquid from upstream of said dialyzer and treated liqdid from downstream of said dialyzer, said detector being connected with said evaluation unit for conveying representations alternately of electrolyte contents of untreated liquid upstream of said dialyzer and of electrolyte contents of treated liquid downstream of said dialyzer.

13. The apparatus according to claim 12, wherein a (68) is branched on a line (30 connecting said dialysis solution producing unit with said dialyzer and a line (70) is branched on a line (44) downstream of said dialyzer; said line (68) and said line (70) being combined in a line (72) connected with said single detector.

14. The apparatus according to claim 13, wherein said line (68) is equipped with a first shut-off valve and said line (70) is equipped with a second shut-off valve said first and second shut-off valves to be activated alternately.

15. The apparatus according to claim 13, further including a storage tank (82) having at least one ventilation aperture (80), said storage tank being coupled to said line (72).

16. The apparatus according to claim 12, wherein said single detector is combined with a temperature detector.

17. The apparatus according to claim 12 further including a unit for forming a difference value wherein aid evaluation unit is connected with said difference value forming unit.

* * * * *